US00RE40862E

(19) United States
(12) Reissued Patent
Flack et al.

(10) Patent Number: US RE40,862 E
(45) Date of Reissued Patent: Jul. 21, 2009

(54) GOSSYPOLONE FOR THE TREATMENT OF CANCER

(75) Inventors: Mary R. Flack, Ann Arbor, MI (US); Richard Knazek, Mount Airy, MD (US); Marcus Reidenberg, Scarsdale, NY (US)

(73) Assignee: The United States of America as represented by the Department of Health and Human Services, Washington, DC (US)

(21) Appl. No.: 11/581,734

(22) Filed: Oct. 16, 2006

Related U.S. Patent Documents

Reissue of:
(64) Patent No.: 6,114,397
Issued: Sep. 5, 2000
Appl. No.: 08/379,872
Filed: Jan. 27, 1995

U.S. Applications:
(60) Continuation of application No. 10/806,088, filed on Mar. 22, 2004, which is a division of application No. 07/551,353, filed on Jul. 12, 1990, now Pat. No. 5,385,936.

(51) Int. Cl.
*A61K 31/12* (2006.01)

(52) U.S. Cl. ..... 514/682; 514/700
(58) Field of Classification Search ..... 514/682
See application file for complete search history.

(56) References Cited

U.S. PATENT DOCUMENTS

| | | | |
|---|---|---|---|
| 4,297,341 | A | 10/1981 | Waller et al. |
| 4,806,568 | A | 2/1989 | Vander Jagt et al. |
| 5,026,726 | A | 6/1991 | Jagt et al. |
| 5,260,327 | A | 11/1993 | Kim et al. |
| 5,759,837 | A | 6/1998 | Kuhajda et al. |
| 6,576,660 | B1 | 6/2003 | Liao et al. |
| 6,608,107 | B2 | 8/2003 | Wong et al. |

FOREIGN PATENT DOCUMENTS

| | | |
|---|---|---|
| CN | 87105990 | 8/1992 |
| JP | H1-132542 | 5/1989 |
| JP | 1-132542 A | 5/1989 |

OTHER PUBLICATIONS

Sausville et al. Cancer Research, 2006, vol. 66, pp. 3351–3354.*

The Merck Manual of Diagnosis and Therapy. 17th Edition, 1999, pp. 216–218.*

Gura et al. Systems for Identifying new drugs are often faulty. Science, 1997, 278:1041–1042.*

Johnson et al. Relationships between drug activity in NCI preclinical in vitro and in vivo models and early clinical trials. British J. of Cancer, 2001, 84(10):1424–1431.*

Band et al., "Antiproliferative Effect of Gossypol and Its Optical Isomers on Human Reproductive Cancer Cell Lines," *Gynecologic Oncology,* 32, 273–277 (1989).

Band et al., "Cytocidal Effects of Gossypol and Its Optical Isomers on Reproductive Cancer Cell Lines," *Gynecologic Oncologists,* 23 (2), 261 (1986).

Benz et al., "Biochemical Correlates of the Antitumor and Antimitochondrial Properties of Gossypol Enantiomers," *Molecular Pharmacology,* 37, 840–847 (1990).

Benz et al., "Gossypol Enantiomers (+, −) Differentially Uncouple Tumor Mitochondria, Block Glutathione–S–Transferase Activity, and Inhibit Cellular Proliferation," *79th Annual Meeting of the American Association for Cancer Research, Proceedings,* 29, 322 (1988).

Benz et al., "Lactic Dehydrogenase Isozymers, $^{31}$P Magnetic Resonance Spectroscopy, and In Vitro Antimitochondrial Tumor Toxicity with Gossypol and Rhodamine–123," *The Journal of Clinical Investigation,* 79 (2), 517–523 (1987).

Benz et al., "Selective Toxicity of Gossypol Against Epithelial Tumors and its Detection by Magnetic Resonance Spectroscopy," *Contraception,* 37 (3), 221–229 (1988).

Bushunow et al., "Gossypol Treatment of recurrent Adult Malignant Gliomas," *J. Neuro–Oncology,* 43, 79–86 (1999).

Cass et al., *J. Agric. Food Chem.,* 52: 5822–5827 (2004).

Cotton Cellulose Chemistr, "Gossypol prepn—from gossypol and anthranilate by alkaline hydrolysis of the anthranilate," SU 212245 (English abstract only) (1973).

De Martino et al., "Electron microscopic and biochemical studies of the effect of Gossypol on Ehrlich ascites tumor cells," *Caryologia,* 35, 114–115 (1982).

Dhaliwal et al., "Cytogenetic Analysis of a Gossypol–Induced Murine Myxosarcoma," *Journal of the National Cancer Institute,* 78 (6), 1203–1209 (1987).

Flack et al., "Treatment of adrenocortical carcinoma with gossypol," *81th Proceedings of the American Association for Cancer Research,* 31, 198 (1990).

Flack et al., "Oral Gossypol in the Treatment of Metastatic Adrenal Cancer," *J. Clin. Endocrinol. Metab.;* 76(4), 1019–1024 (1993).

(Continued)

*Primary Examiner*—Ardin Marschel
*Assistant Examiner*—James D Anderson
(74) *Attorney, Agent, or Firm*—Leydig, Voit & Mayer, Ltd.

(57) ABSTRACT

A method for treating cancer in a human, which comprises administering to the human subject an anti-cancer effective amount of a compound selected from gossypol, gossypol acetic acid, gossypolone, metabolites thereof, or physiologically acceptable salts thereof. Also included is a method for treating cancer in a human which comprises administering to the human subject an anti-cancer effective amount of any of the compounds listed above in combination with an anti-cancer effective amount of other conventional chemotherapeutic agents. Finally, the invention also encompasses a pharmaceutical composition comprising an anti-cancer effective amount of gossypol, gossypol acetic acid, or gossypolone, and an anti-cancer effective amount of a conventional chemotherapeutic agent, or combinations of the latter.

12 Claims, 2 Drawing Sheets

OTHER PUBLICATIONS

Flordi et al., "The Effect of the Association of Gossypol and Lonidamine on the Energy Metabolism of Ehrlich Ascites Tumor Cells," *Experimental and Molecular Pathology,* 38, 322–335 (1983).

Han et al., "Gossypol in the Treatment of Endometriosis and Uterine Myoma," *Contributions to Gynecology and Obstetrics,* 16, 268–270 (1987).

Haspel et al., "Cytocidal Effect of Gossypol on Cultured Murine Erythroleukemia Cells is Prevented by Serum Protein," *The Journal of Pharmacology and Experimental Therapeutics,* 229 (1), 218–225 (1984).

Hei et al., *ACTA Academiae Medicinae Sinicae,* 61(9):527–529 (1981).

Hu et al., "Gossypol Effects on Cultured Normal and Malignant Melanocytes," *In Vitro Cellular & Developmental Biology,* 22 (10), 583–588 (1986).

Huang et al., "Resolution of Racemic Gossypol," *Journal of Ethnopharmacology,* 20, 13–20 (1987).

Ligueros et al., "Gossypol inhibition of mitosis, cyclin D1 and Rb protein in human mammary cancer cells and cyclin–D1 transfected human fibrosarcoma cells," *British J. of Cancer,* 76(1), 21–28 (1997).

Jaroszewski et al., "Action of Gossypol and Rhodamine 123 on Wild Type and Multidrug–resistant MCF–7 Human Breast Cancer Cells: $^{31}$P Nuclear Magnetic Resonance and Toxicity Studies," *Cancer Research,* 50, 6936–6943 (1990).

Jaroszewski et al., Abstract, "Effects of Gossypol On Drug–Sensitive and Drug–Resistant Cancer Cells," *Proc. Am. Assoc. Cancer Res 31*, 377 (1990).

Jingfang et al., "of Gossypol in Mice, Rats and Human Tumor Cell Lines and Its Possible Mechanism," *Acta Academiae Medicinae Sinicae,* 8 (6), 486–489 (1986).

Jolad et al., "Tumor–Inhibitory Agent from *Montezuma speciosissima* (Malvaceae)," *Journal of Pharmaceutical Sciences,* 64 (11), 1889–1890 (1975).

Joseph et al., "Cytotoxicity of enantiomers of gossypol," *The British Journal of Cancer,* 54 (3), 511–513 (1986).

Kable et al., "Potency, Selectivity and Cell Cycle Dependence of Catechols in Human Tumor Cells In Vitro," *Biochem. Pharmacol,* 37, 1711–1715 (1988).

Kai et al., "Resolution of Racemic Gossypol," *Journal of the Chemical Society,* (3), 168–169 (1985).

Keniry et al., "The Effect of gossypol and 6–aminonicotinamide on tumor cell metabolism: A $^{31}$P–Magnetic Resonance spectroscopic study," *Biochemical and Biophysical Research Communications,* 164 (2), 947–953 (1989).

Keniry et al., "Magnetic Resonance Spectroscopy (MRS) and Imaging (MRI) in the Evaluation of Tumor Growth and Chemotherapy Response," *Proceedings, 77th Annual Meeting of the American Association for Cancer Research,* 27, 384 (1986).

Kim et al., "Comparative In Vitro Spermicidal Effects of (±)–Gossypol, (+)–Gossypol, (−)–Gossypol, a Hyperthermic Sensitizer of HeLa Cells," *Cancer Res.,* 45, 6338–6340 (1985).

Kuznetsova et al., "Determination of the cytotoxic effect and antitumor activity of gossypol and some of its derivatives," Deposited Doc. (1979), Viniti 409–79, 7 pp. (Abstract Only).

Kuznezova et al., "Measurement of Cytotoxic effects and anti–cancer properties of gossypol and its derivatives," *Pharmacol. Toxicol.,* 1–7 (1979) (English abstract only).

Matlin et al., "Large–Scale Resolution of Gossypol Enantiomers for Biological Evaluation," *Contraception,* 37 (3), 229–237 (1988).

McClarty et al., "Ribonucleotide Reductase: An Intracellular Target for the Male Antifertility Agent, Gossypol," *Biochem. Biophys. Res. Commun.,* 133, 300–305 (1985).

McSheehy et al., "Gossypol, a cytoxic agent, may uncouple respiration of Ehrlich Ascites tumour cells," *Biochemical Society Transactions,* 16 (4), 616–617 (1988).

Meiling, "Gossypol Treatment for Menopausal Functional Bleeding, Myoma of Uterus and Endometriosis—Preliminary Report," *Acta Academiae Medicinae Sinicae,* 2 (3), 168–170 (1980).

Molla et al., Influence of 5–Hydroxytryptamine on the Combination Effect of Lonidamine or Gossypol and Hyperthermia on Ehrlich Tumour In Vivo, *Anticancer Res.,* 7, 361–364 (1987).

Moss et al., "Initiation and Proliferation of Gossypol–Producing Cotton Hairy Roots," 2005 Beltwide Cotton Conferences, New Orleans, Louisiana, p. 2092 (Jan. 4–7, 2005).

Nayak et al., "Induction of Sister Chromatid Exchanges and Chromosome Damage by Gossypol in Bone Marrow Cells of Mice," *Teratogenesis, Carcinogenesis, and Mutagenesis,* 6 (2), 83–91 (1986).

Ohuchi et al., "Inhibition by gossypol of tumor promoter–induced arachidonic acid metabolism in rat peritoneal macrophages," *Biochimica et Biophysica Acta,* 971, 85–91 (1988).

Pirogov et al., "Postoperative Bronchopleural Complications in Combined Treatment of Pulmonary Cancer," *Voprosy Onkologii,* 20 (6), 24–28 (1974).

Polsky et al., "Inactivation of Human Immunodeficiency Virus In Vitro by Gossypol," *Contraception,* 39(6), 579–587 (1989).

Qian et al., "Gossypol: A Potential Antifertility Agent for Males," *Annual Review of Pharmacological Toxicology,* 24, 329–360 (1984).

Rao et al., "Antitumor effects of gossypol on murine tumors," *Cancer Chemotherapy. Pharmacology,* 15, 20–25 (1985).

Reidenberg, "Studies of Gossypol in the Treatment of Cancer," *Reproductive Medicine: A Millennium Review,* New York and London Pantheon, 305–308 (1999).

Sampath et al., "A Rapid Procedure for the Resolution of Racemic Gossypol," *Journal of the Chemical Society,* (9), 649–650 (1986).

Senzer, "Hyperthermia: Chemotherapeutic and biologic response modifications," *Strahlenther. Onkol.,* 165, 729–733 (1989).

Stipanovic et al., "Occurrence of (+)– and (−)–Gossypol in Seed from Wild Species of Gossypium," 2005 Beltwide Cotton Conferences, New Orleans, Louisiana, p. 900 (Jan. 4–7, 2005).

Stipanovic et al., *J. Agric. Food Chem.,* 53(16): 6266–6271 (2005).

Tanphaichitr et al., "Direct Effect of Gossypol on TR–ST Cells: Perturbation of Rhodamine 123 Accumulation in Mitochondria," *Biology of Reproduction,* 31, 1049–1060 (1984).

Thoenes et al., "Cytotoxic Effects of Adriamycin, Bleomycin, Gossypol and Hydroxyanisol to Cultured Human Malignant Melanoma Cells," *Journal of Cancer Research and Clinical Oncology,* 113, S 46 (1987).

Tso, "Gossypol Inhibits Ehrlich Ascites Tumor Cell Proliferation," *Cancer Letters,* 24, 257–261 (1984).
Tuszynski et al., "Differential Cytotoxic Effect of Gossypol on Human Melanoma, Colon Carcinoma, and Other Tissue Culture Cell Lines," *Cancer Research,* 44, 768–771 (1984).
Van Poznak et al., *Breast Cancer Research and Treatment,* 66, 239–248 (2001).
Vermel et al., "Antitumor Activity of Gossypol in Experiments on Transplanted Tumours," *Voprosy Oncoligii,* 9 (12), 30–43 (1963).
Vermel, "The Search for Antitumour Substances of Plant Origin," *Acta Unio Internationalis Contra Cancrum,* 20, 211–213 (1964).
Vermel et al., *Voprosy Onkologii 10,* 88–97 (1964).
Wang et al., "Effect of Gossypol on DNA Synthesis and Cell Cycle Progression of Mammalian Cells in Vitro," *Cancer Research,* 44, 35–38 (1984).
Wu et al., *Acta Academiae Medicinae Sinicae,* 8(6):489 (Dec. 1986).
Wu et al., "Pharmacokinetics of (±)–, (+)–, and (−)–gossypol in humans and dogs," *Clinical Pharmacology & Therapeutics,* 39 (6), 613–618 (1986).
Wu et al., "An in Vitro and in Vivo Study of Antitumor Effects of Gossypol on Human SW–13 Adrenocortical Carcinoma," *Cancer Research,* 49, 3754–3758 (1989).
Wu et al., "In vitro antitumor activity of gossypol alone or in combination with amsacrine," *European Journal of Pharmacology,* 183 (2), 230 (1990).
Wu et al., *J. Chromatography,* 433, 141–148 (1988).
Xu, *J. of Science and Medicine of Jinan Univ.,* 2:40–42 (Jun. 1987).
Xueqing et al., "Clinical Observation and Experimental Study of Gossypol in Treatment of Dysfunctional Menorrhagia, Endometriosis and Fibromyoma of Uterus," *Chinese J. Interger. Trad. Western Med.,* 8, 197 & 216–217 (1988).
Yerukhimov. "Treatment of Bladder Tumors with Gossipol and Ionol in Combination with Surgical Intervention," *Voprosy Onkologii,* 12 (2), 29–34 (1966).
Yikang et al., "Studies on Resolution of Racemic Gossypol: Separation of Hexaacetates of S–1–Methylphenethylamino Derivative of (±) Gossypol," *Scientia Sinica,* 30 (3), 297–303 (1987).
Yu, "Probing into the Mechanism of Action, Metabolism and Toxicity of Gossypol by Studying Its (+)– and (−)– Stereoisomers," *Journal of Ethnopharmacology,* 20, 65–78 (1987).
Zheng et al., "Studies on the Resolution of Racemic Gossypol: IV. Use of Threo(−) or (+)–1–(p–Nitrophenyl)–1,3–Dihydroxypropylamine–2 as the Resolving Agent," *Acta Pharmaceutica Sinica,* 25 (6), 430–434 (1990).
Zhang et al., *Acta Academiae Medicinae Sinicae,* 7(5):385–387 (Oct. 1985).
Zhang et al., *Acta Academiae Medicinae Sinicae,* 8(6):486–488 (Dec. 1986).
Zhou et al., *Contraception,* 37(3): 239–245 (1988).
Rao et al. (1985) *Cancer Chemother. Pharmacol.* 15:2–25.*
Kim et al, Contraception 312 : 5966–72 (1984.*

* cited by examiner

GOSSYPOLONE FOR THE TREATMENT OF CANCER

Matter enclosed in heavy brackets [ ] appears in the original patent but forms no part of this reissue specification; matter printed in italics indicates the additions made by reissue.

*CROSS-REFERENCE TO RELATED APPLICATIONS*

*Notice: More than one reissue application has been filed for the reissue of U.S. Pat. No. 6,114,397. The reissue applications are U.S. patent application Ser. Nos. 11/581,734 (the present application), filed Oct. 16, 2007, and 10/806,088, filed Mar. 22, 2004. U.S. patent application Ser. No. 08/379,872, filed Jan. 27, 1995, issued as U.S. Pat. No. 6,114,397, which is a divisional of U.S. patent application Ser. No. 07/551,353, filed Jul. 12, 1990, issued as U.S. Pat. No. 5,385,936.*

BACKGROUND OF THE INVENTION

1. Field of the Invention

The present invention is related to the use of gossypol and related compounds as anti-tumor agents effective against human cancers including, but not limited to, adrenocortical carcinoma, uterine, cervical, ovarian and testicular carcinoma, breast cancer, and carcinoid tumors.

2. Description of the Related Art

Gossypol is a double biphenolic compound derived from crude cottonseed oil which has been shown to inhibit spermatogenesis, and which has been used extensively as a male contraceptive in China.

While gossypol has been shown to retard the growth of some cancers in nude mice, its effects vary widely from species to species (Qian, S Z (1984) Ann. Rev. Pharmacol. Toxicol. 24: 329–60; Kim et al. (1984) Contraception 312: 5966–72). The effect of gossypol on the mitochondrial accumulation of rhodamine has been shown to be lower in magnitude in human cells than in rat testicular tumor cells (Tanphaichitr et al. (1984) Biol. of Reprod. 31: 1049–1060). Furthermore, closely related compounds such as mitotane (ortho-para'-DDD), a biphenolic compound which has been used to treat adrenal cancer, are only of limited effectiveness in treating cancer in humans. In addition, the side effects produced at the doses required for response can be debilitating, and include anorexia, nausea, vomiting, and dizziness. Conventional chemotherapy such as with cytoxan, adriamycin, 5FU, and other agents has a low response rate, and side effects such as hair loss, bone marrow suppression, nausea, vomiting, and heart failure. Clearly, an alternate or adjuvant therapy with less toxic side effects is desirable.

The use of gossypol and related compounds as anti-tumor agents against cancers in humans has yet to be reported.

SUMMARY OF THE INVENTION

The present invention relates to the use of compounds with the following formula:

Gossypol

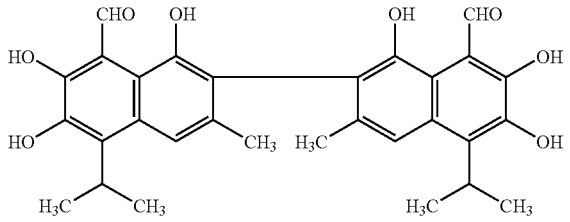

in the treatment of human cancer, including treatment of adrenal, ovarian, thyroid, testicular, pituitary, prostate, and breast tumors, as well as other types of tumors.

Pharmaceutical compositions useful in the present method of treatment include the formulation of gossypol and gossypol acetic acid, which contain both the positive and negative enantamers of gossypol, and formulations containing only one enantamer, as well as any physiologically acceptable salts, for either enteral or parenteral use. Such compositions also include those containing gossypolone. These compounds may be used alone, in combination with one another, or in combination with other conventional chemotherapeutic pharmaceutical compositions. The invention also includes the use of any metabolic products generated from gossypol which have anti tumor activity.

As compared to conventional therapies, the use of gossypol and the related compounds noted above to treat human cancers is associated with milder side effects. These include mild fatigue, muscle tremor, dry mouth, dry skin, and occasional nausea. These are well tolerated, and patients are able to continue their normal activities. In addition, conventional chemotherapeutic agents are associated with a high degree of drug resistance. As discussed below, anti-tumor gossypol therapy has been demonstrated to be effective in patients who exhibit resistance to conventional anti-tumor agents.

As gossypol is taken up into a number of human endocrine tissues, including the adrenal gland, testis, ovary, uterus, thyroid and pituitary, it can be used in the treatment of cancers of these organs, and against carcinoid tumors which are tumors of neuroendocrine tissue which may be located in the lung, pancreas, or gastrointestinal tract.

As previously noted, gossypol has been found to retard the growth of some cancers in nude mice. However, its effects vary widely from species to species. It could not be assumed, therefore, that the anti-cancer effects seen in animals would be seen in humans. A further unexpected feature associated with the use of gossypol to treat cancer in human subjects as opposed to that in animals is that in the latter, higher doses of gossypol (e.g., 0.8 or 1.6 mg/mouse) have been shown to be lethal (Rao et al. (1985) Cancer Chemother. Pharmacol. 15: 20–25), negating any potential benefit of the drug in slowing cancer growth and prolonging survival. The present inventors have shown that the anti-tumor effect of gossypol in humans occurs at doses which are approximately one tenth of those effective in animals, i.e., 1 mg/kg/d vs. 10 mg/kg/d. Toxicity in humans begins to occur at doses greater than 1–2 mg/kg/d. Therefore, the studies of gossypol in animals do not make the use of gossypol for the treatment of cancer in humans, at appropriate doses, obvious in the latter.

Existing therapies for the treatment of human tumors, including adrenal, ovarian, thyroid, testicular, pituitary, prostate, and breast tumors, are multiple, including 5-fluorouracil, adriamycin, cytoxan, cisplatin, etoposide, suramin, and ortho-para'DDD (mitotane). These agents have a partial response rate of less than 20% for adrenocortical carcinoma, and less than 50% for other cancers. The toxicity of these agents, which is not exhibited by gossypol, includes myelosuppression, nausea, vomitting, anorexia, hair loss, cardiac failure and neurotoxicity. Thus, there is a need for anti-tumor agents with less toxicity which have activity against these tumors, and others, which are resistant to existing agents.

Gossypol is a human anti-tumor agent which causes fewer side effects than such existing treatments.

Accordingly, it is an object of the present invention to provide a method for treating cancer in a human, which comprises administering to the subject an anti-cancer effective amount of gossypol, gossypol acetic acid, or gossypolone.

Another object of the present invention is to provide a method for treating cancer in a human which comprises administering to the subject an anti-cancer effective amount of gossypol, gossypol acetic acid, or gossypolone, and an anti-cancer effective amount of 5-fluorouracil, adriamycin, cytoxan, cisplatin, etoposide, suramin, mitotane, or other conventional chemotherapeutic agent, or combinations of these compounds.

A further object of the present invention is to provide a pharmaceutical composition comprising an anti-cancer effective amount of gossypol, gossypol acetic acid, or gossypolone, and an anti-caner effective amount of the compounds listed above, or combinations of these compounds.

Further scope of the applicability of the present invention will become apparent from the detailed description and drawings provided below. However, it should be understood that the detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following descriptions taken in conjunction with the accompanying drawings, in which.

DETAILED DESCRIPTION OF THE INVENTION

Media, Reagents, and Cells

Dulbecco's minimal Eagle's medium, fetal calf serum, glutamine, penicillin, and streptomycin were purchased from Quality Biological, Inc. (Gaithersburg, Md.); Hanks' balanced salt solution and trypsin-EDTA were obtained from Gibco Laboratories (Grand Island, N.Y.). 1,6-Diphenylhexatriene and tetrahydrofuran were from Aldrich Chemical Co., Inc. (Milwaukee, Wis.). Gossypol and gossypol acetic acid were gifts from the National Research Institute for Family Planning (Beijing, China). The established line of small cell human adrenocortical carcinoma (SW-13) was purchased from the American Type Culture Collection (Rockville, Md.).

In Vitro Gossypol Treatment

Cell Proliferation

Sw-13 cells were seeded in a 25-$cm^2$ tissue culture flask (Costar, Cambridge, Mass.) at densities of $1\times10^4$ cells/5 ml of Dulbecco's minimal Eagle's medium, supplemented with 10% fetal calf serum, 100 ug/ml streptomycin, 100 units/ml penicillin, and 2 mM glutamine. The cells were grown in a humidified, 37° C. incubator with a 5% $CO_2$/95% air atmosphere. A gossypol stock solution in absolute ethanol was added to the culture medium to yield final concentrations of 0, 0.5, 5, and 50 uM gossypol with a 0.1% final ethanol concentration. After 1, 2, 4, or 6 days of incubation, the culture medium containing a few floating cells was removed. Adherent cells were typsinized (0.1% trypsin, w/v) and counted using a hemocytometer. Cell viability was determined by trypan blue exclusion.

Figure 1:
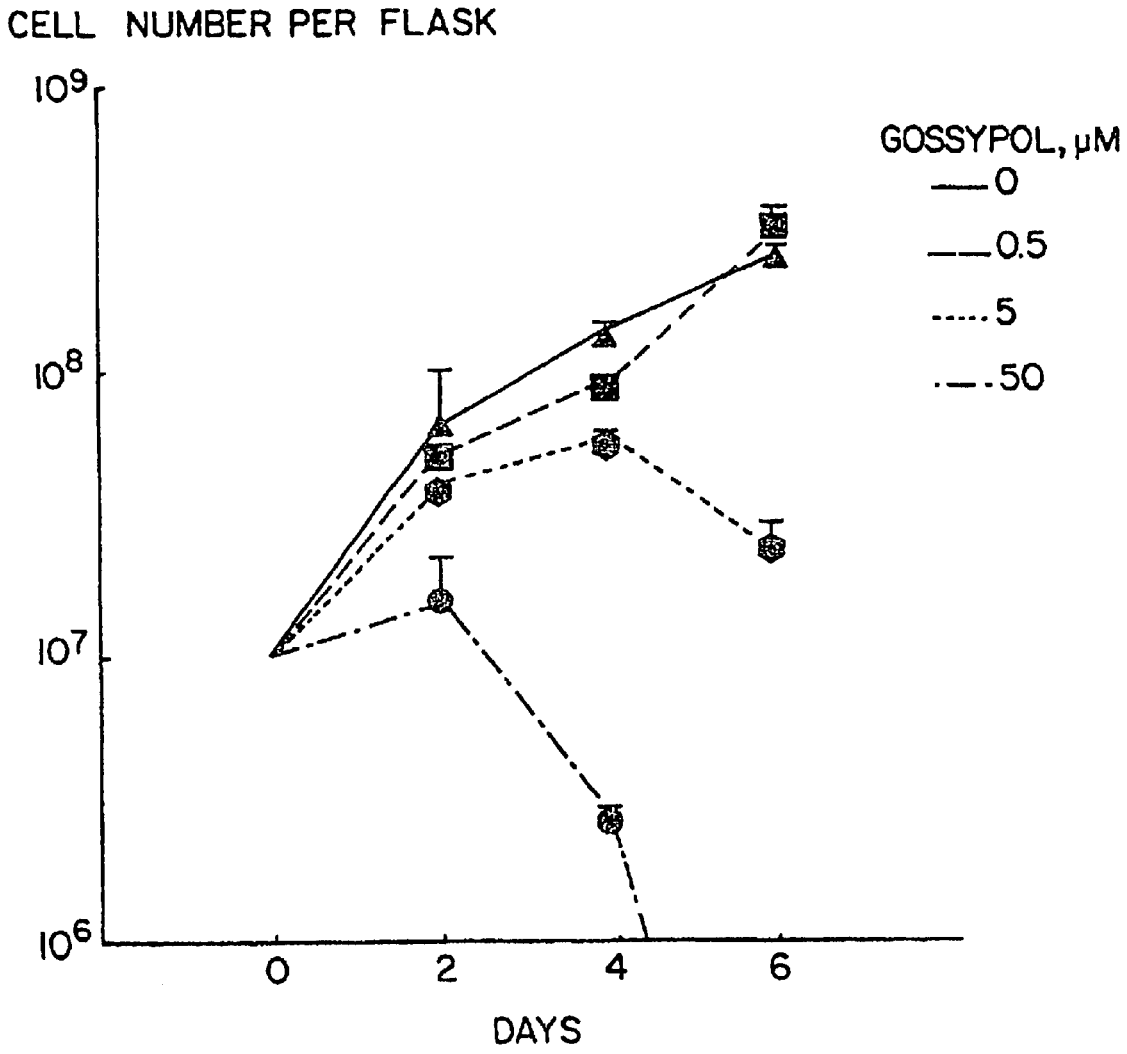
FIG. 1 shows the effects on proliferation of SW-13 cells of 0, 0.5, 5, and 50 uM gossypol during prolonged exposure. SW-13 cells were seeded ($1\times10^4$ cells) into 25 $cm^2$ tissue culture flasks in Dulbecco's minimal Eagle's medium supplemented with fetal calf serum (10%), 100 ug/ml streptomycin, 100 units/ml penicillin, and 2 mM glutamine. Exposure to 5 and 50 uM gossypol inhibited cell proliferation.

As shown in FIG. 1, exposure of SW-13 cells to 5 and 50 uM gossypol inhibited cell proliferation.

In Vivo Gossypol Treatment

Nude Mice

Nude mice (Charles River, Kingston, N.Y.) weighing 20–35 g were caged in a temperature-controlled (26–28° C.), 12 h/12 h light/dark animal room. A microporous cage bonnet served as an effective protective barrier between the animal and the outside environment. In addition, the room was continuously purged with High Efficiency Particle Attenuator-filtered air. The cages, feeders, and water bottles were designed to make standard mouse chow and water readily available while minimizing the opportunity for the transfer of communicable pathogens.

Transplantation of SW-13 Cells

Forty-nine adult male nude mice weighing 20–24 g were divided into two groups of 24 for control and 25 for gossypol treatment. Gossypol acetic acid was suspended in 75% ethanol for 24 h, then evaporated in vacuum chamber with desiccant, and finally suspended in sterilized 0.25% carboxymethylcellulose carrier. The gossypol-treated group received 30 mg gossypol/kg body weight/day via an orogastric tube. Control mice were fed an equal volume of carrier. Body weights were measured weekly. At the end of the first week of gossypol treatment, $2\times10^6$ SW-13 cells were injected s.c. on the back of these mice, which continued to receive gossypol or carrier for 5 additional weeks. Tumor surface areas (length×width, $cm^2$) were measured daily. After 5 weeks, the animals were decapitated.

Another experiment was designed wherein 48 adult male nude mice weighing 25–35 g were injected s.c. with $2\times10^6$ SW-13 cells. One month later, the animals were divided into two groups of 24. There were 7 nude mice without visible tumors in each group. The gossypol treated animals received 30 mg gossypol acetic acid/kg body weight/day whereas control animals were fed an equal volume of carrier. Body weigths and tumor sizes (lengths×width, $cm^2$) were measured weekly. During the 12th week of treatment, 5 control animals died. Since it appeared unlikely that the remaining control animals would survive for another week, they were then sacrificed. Autopsies were performed on all animals including those that died during the study period. Internal organs were examined for the presence of gross tumor.

Statistical Analysis

Data are expressed as the mean±SD unless otherwise indicated. Statistical comparisons were made using an unpaired Student's t test.

Effect of Gossypol on SW-13 Tumor Bearing Nude Mice

In this experiment, nude mice had been given s.c. injections of SW-13 adrenocortical carcinoma 1 month prior to initiation of the treatment with either gossypol or carrier.

During the subsequent 12 weeks of treatment, there were 10 deaths in the control group: 4 had apparent ascites, were jaundiced, and had large intraperitoneal tumors; 2 suffered from hind leg paralysis due to a tumor metastatic to the spinal column; 2 animals had small tumors, but both showed significant weight loss; 2 had demonstrated neither visible tumors nor an obvious cause of death. In contrast, only two deaths were observed in the gossypol-treated group, one of them having ascites while the other had no apparent tumor at autopsy. Each treated mouse in the group received a total dose of 81.9 mg gossypol during the 12-week period.

As in the previous study, 12 weeks of gossypol treatment had no significant effect on body weights. At the end of the study period, the body weights in both groups were 32.2±3.8 and 30.9±3.6 g for the control and gossypol-treated groups, respectively. After 12 weeks of treatment, the tumor prevalence had risen from 71 to 83% in the control group, while the gossypol-treated group exhibited a decrease in tumor prevalence from 71% to 54%. This was accompanied by the death of 41.6% of the controls and 8.3% of the gossypol-treated group (Table 1).

TABLE 1

Effect of gossypol on tumor prevalence and mortality in mice having preexisting tumors

| | Control (%) | | Gossypol (%) | |
|---|---|---|---|---|
| Week | Prevalence of tumor | Total deaths | Prevalence of tumor | Total deaths |
| 0 | 71 | 0 | 72 | 0 |
| 1 | 75 | 0 | 63 | 0 |
| 2 | 83 | 0 | 50 | 0 |
| 3 | 83 | 0 | 54 | 0 |
| 4 | 83 | 0 | 50 | 0 |
| 5 | 83 | 0 | 58 | 0 |
| 6 | 83 | 0 | 58 | 0 |
| 7 | 83 | 8.3 | 58 | 0 |
| 8 | 83 | 8.3 | 58 | 0 |
| 9 | 83 | 12.5 | 54 | 0 |
| 10 | 83 | 16.7 | 54 | 0 |
| 11 | 83 | 20.8 | 54 | 0 |
| 12 | 83 | 41.6 | 54 | 8.3 |

The mean tumor sizes of the control and the gossypol treated groups were shown as a function of duration of treatment in Table 2. The slight decline in the mean tumor size observed towards the end of the study period was due to the fact that the majority of the control mice that died during the study has large tumors.

TABLE 2

Effect of gossypol on mean tumor size

| | Mean tumor size ($cm^2$) (mean ± SE) | |
|---|---|---|
| Week | Control | Gossypol |
| 0 | 0.09 ± 0.02 | 0.08 ± 0.02 |
| 1 | 0.22 ± 0.05 | 0.07 ± 0.02 |
| 2 | 0.28 ± 0.06 | 0.12 ± 0.04[a] |
| 3 | 0.35 ± 0.07 | 0.15 ± 0.05[a] |
| 4 | 0.50 ± 0.11 | 0.20 ± 0.07[a] |
| 5 | 0.66 ± 0.17 | 0.28 ± 0.08[a] |
| 6 | 0.87 ± 0.22 | 0.32 ± 0.10[a] |
| 7 | 0.97 ± 0.25 (n = 23) | 0.38 ± 0.12[a] |
| 8 | 1.16 ± 0.33 (n = 22) | 0.45 ± 0.14[a] |

TABLE 2-continued

Effect of gossypol on mean tumor size

| | Mean tumor size ($cm^2$) (mean ± SE) | |
|---|---|---|
| Week | Control | Gossypol |
| 9 | 1.07 ± 0.34 (n = 20) | 0.50 ± 0.15[a] |
| 10 | 1.14 ± 0.36 (n = 20) | 0.59 ± 0.18[a] |
| 11 | 1.39 ± 0.41 (n = 19) | 0.68 ± 0.21[a] |
| 12 | 0.96 ± 0.21 (n = 15) | 0.81 ± 0.25 (n = 22) |

[a]$P < 0.05$, control compared to gossypol treated group; n = 24 unless otherwise indicated.

Figure 2:
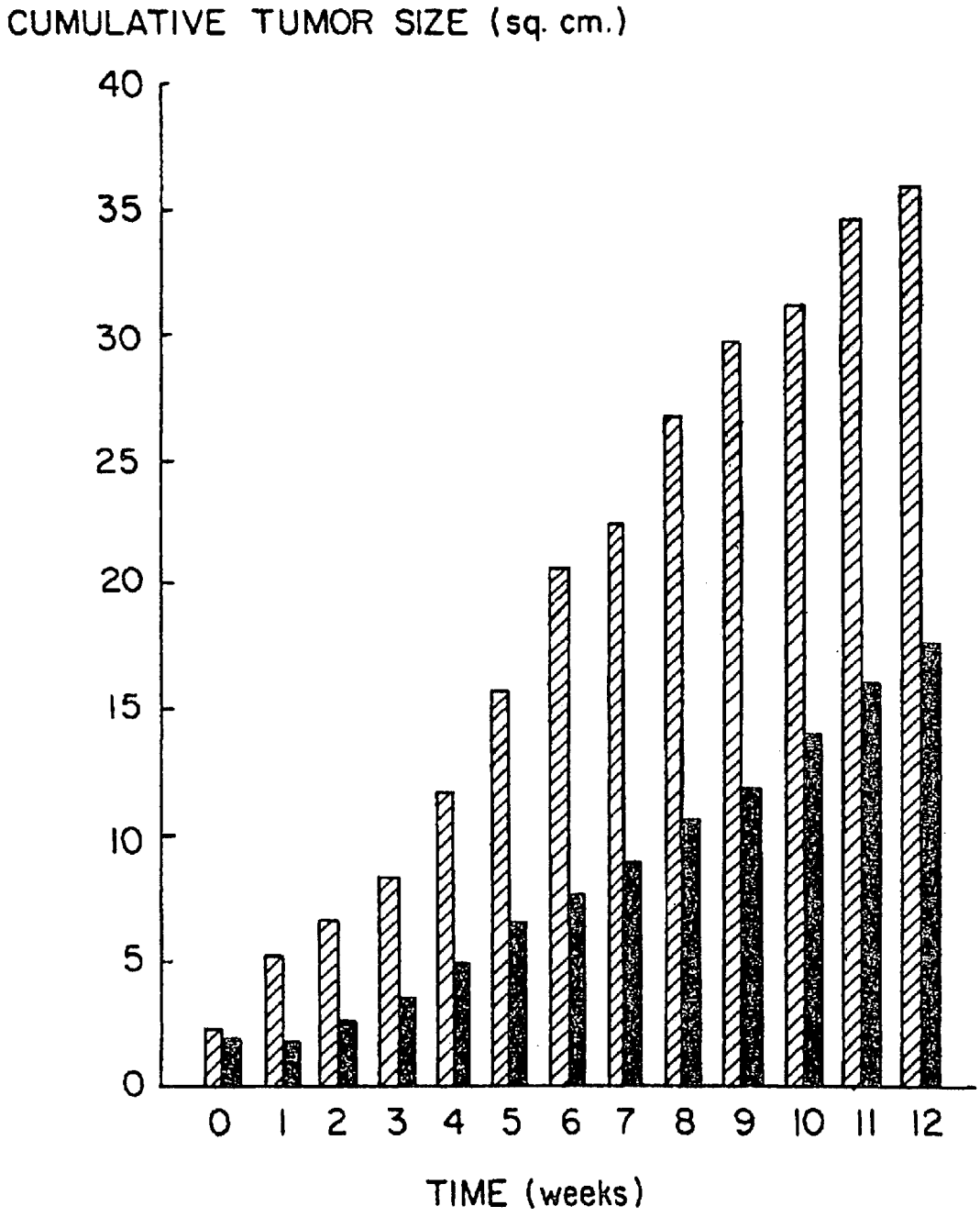
FIG. 2 shows the effect of gossypol on the cumulative surface area of SW-13 human adrenocortical carcinoma in nude mice. Gossypol and placebo were given one month after the injection of tumor cells. Gossypol (mg/kg/day): ■, ○; ■, 30.

The total tumor burden of the two groups rose during the treatment period, the controls reaching a value twice that of the gossypol group at the 12th week (FIG. 2).

Treatment of Human Metastatic Adrenal Cancer

Previous medical therapy for metastatic adrenocortical carcinoma has been largely unsuccessful. Based on the growth inhibitory effect of gossypol on SW-13 human adrenocortical tumors in vivo in nude mice, discussed above, the effect of oral gossypol treatment on metastatic adrenal cancer in a human patient was investigated.

A 36 year old man presented with a left sided adrenocortical carcinoma, 26×13 cm, invading the kidney and inferior vena cava. Surgical excision of all visible tumor was performed, and the patient was started on mitotane postoperatively. Pulmonary metastases were found six months later, which were resected. Six month following thoracotomy, multiple hepatic metastases were found. His tumor progressed despite treatment with Suramin and adriamycin/VP16.

At the time of gossypol treatment, the patient had nocturnal dyspnea requiring supplemental oxygen therapy, markedly decreased exercise tolerance, persistent abdominal pain, and pedal edema. Physical examination revealed a cushingoid man with a blood pressure of 150/90, bilateral tender gynecomastia, a liver span of 14 cm, abdominal distension and fluid wave, and bilateral pitting edema to the knee.

Gossypol acetic acid, 10 mg compressed tablet, was given orally at a dose of 20 mg/d which was increased by 10 mg/d every three days to a dose of 50 mg/d.

During gossypol treatment, the patient experienced fatigue, xerostomia, tremor, and trasnminitis. After three weeks of gossypol treatment, CT scans showed complete resolution of pulmonary metastases and greather than 50% decreased in the size of the hepatic metastases, and an improvement in abdominal pain, ascites, and pulmonary function.

A summary of the results obtained in this and other human subjects during a phase I clinical trail of oral gossypol for the treatment of metastatic adrenocortical carcinoma is presented in Table 3.

TABLE 3

Summary of Preliminary Results of Phase 1 Clinical Trial of Oral Gossypol for Adrenocortical Cancer

| Age/Sex | Site | Dose | Duration | Level | Side Effects | Response |
|---|---|---|---|---|---|---|
| 36/M* (*Patient described above) | Lung Liver | 40-60 mg/d | 28 weeks | 463 ng/dl | Xerostomia Fatigue Gyneco-mastia Trans-aminitis | Partial Response |

TABLE 3-continued

Summary of Preliminary Results of Phase 1 Clinical Trial of Oral Gossypol for Adrenocortical Cancer

| Age/Sex | Site | Dose | Duration | Level | Side Effects | Response |
|---|---|---|---|---|---|---|
| 26/M | Lung Liver | 70 | 3 weeks | 1,025 | Xerostomia Nausea Trans-aminitis | Pro-gression |
| 52/F | Abdo-men | 40 | 6 weeks | 444 | Xerostomia Fatigue Nausea | Partial Response |
| 34/M | Abdo-men Liver | 40-50 | 12 weeks | 291 | Xerostomia Fatigue Nausea | Stabili-zation |
| 27/M | Abdo-men Pelvis | 50 | 6 weeks | 229 | Xerostomia Fatigue | Pro-gression |

Of these five patients, two exhibited partial tumor responses, one has stable disease, and two showed tumor progression.

Pharmaceutical Compositions and Modes of Administration of Gossypol and Related Compounds The method of the present invention includes the administration of gossypol, gossypol acetic acid, or gossypolone, alone or in combination with one another and/or other conventional chemotherapeutic agents, and a pharmaceutically acceptable excipient, to a human subject.

In the methods according to the present invention pharmaceutical compositions containing compounds according to the present invention are administered in an effective amount to a human host for the treatment of a variety of human cancers including adrenal, ovarian, thyroid, testicular, pituitary, prostate, and breast cancer.

In administering gossypol and related compounds for the treatment of cancer by the methods of the present invention, certain pharmaceutical compositions, doses, routes of administration, and desired blood levels may be employed. These are summarized in the table below. In each case, the indicated dose and blood level are approximate, e.g., for oral administration of gossypol acetic acid(+)-compressed tablet, the does may be from about 40 to about 100 mg/d, and the desired blood level may be from about 400 to about 800 ng/dl.

TABLE 4

Pharmaceutical Formulations, Doses, Routes of Administration, and Effective Blood Levels of Gossypol and Related Compounds for the Treatment of Human Cancer.

| Formulation | Route | Dose | Blood Level |
|---|---|---|---|
| Gossypol acetic acid (+)-compressed tablet | Oral | 40-100 mg/d | 400-800 ng/dl |
| Gossypol acetic acid (+)-suppositories | Rectal, vaginal | 40-140 mg/d | 400-1000 ng/dl |
| Gossypol(+)-PVP and physiologic salts | Parent-eral | 1-2 mg/kg/d | 400-1000 ng/dl |
| Gossypol acetic acid (x)-compressed tablet | Oral | 40-100 mg/d | 400-800 ng/dl |
| Gossypol acetic acid (x)-suppositories | Rectal, vaginal | 40-140 mg/d | 400-1000 ng/dl |
| Gossypol(x)-PVP and physiologic salts | Parent-eral | 1-2 mg/kg/d | 400-1000 ng/dl |
| Gossypol(−)-tablet | Oral | 20-100 mg/d | 200-1000 ng/dl |
| Gossypol(−)-suppositories | Rectal | 40-140 mg/d | 200-1000 ng/dl |

TABLE 4-continued

Pharmaceutical Formulations, Doses, Routes of Administration, and Effective Blood Levels of Gossypol and Related Compounds for the Treatment of Human Cancer.

| Formulation | Route | Dose | Blood Level |
|---|---|---|---|
| Gossypol(−)-PVP and physiologic salts | Parent-eral | 1-2 mg/kg/d | 200-1000 ng/dl |
| Gossypolone tablet | Oral | 50-200 mg/d | 400-1000 ng/dl |
| Gossypolone suppositories | Rectal, vaginal | 50-200 mg/d | 400-1000 ng/dl |
| Gossypolone PVP and physiologic salts | Parent-eral | 1-5 mg/kg/d | 400-1000 ng/dl |

When administered orally, the drug may be taken in divided doses, two to three times a day.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for treating a cancer in a human, wherein the cancer is susceptible to treatment with [gossypol, a physiologically acceptable salt of gossypol,] gossypolone, a physiologically acceptable salt of gossypolone, or any combination thereof, which method comprises:

administering to said human an anti-cancer effective amount of at least one compound selected from the group consisting of [gossypol, a physiologically acceptable salt of gossypol,] gossypolone, and a physiologically acceptable salt of gossypolone, [and] *with* a pharmaceutically acceptable carrier*, wherein the cancer is selected from the group consisting of adrenal, ovarian, thyroid, testicular, pituitary, prostate, or breast cancer*.

[2. The method of claim 1, wherein said cancer is adrenal, ovarian, thyroid, testicular, pituitary, prostate, or breast cancer.]

3. The method of claim [2]*1*, wherein said cancer is adrenal cancer.

4. The method of claim 1, wherein the blood concentration of said compound is [400]*200*–1000 ng/dl.

5. The method of claim 4, wherein said compound is gossypolone[or a physiologically acceptable salt of gossypolone].

6. The method of claim [5]*4*, wherein said gossypolone or physiologically acceptable salt of gossypolone is administered orally, rectally or vaginally at a dose of 50–200 mg/d.

7. The method of claim [5]*4*, wherein said gossypolone or physiologically acceptable salt of gossypolone is administered parenterally at a dose of 1–5 mg/kg/d.

[8. A method for treating a cancer in a human, wherein the cancer is susceptible to treatment with gossypol, a pharmaceutically acceptable salt of gossypol, or a combination thereof, which method comprises:

administering to said human an anti-cancer effective amount of at least one compound selected from the group consisting of gossypol and a physiologically acceptable salt thereof, and a pharmaceutically acceptable carrier.]

[9. The method of claim 8, wherein said cancer is adrenal, ovarian, thyroid, testicular, pituitary, prostate or breast cancer.]

[10. The method of claim 8, wherein said cancer is adrenal cancer.]

[11. The method of claim 8, wherein the blood concentration of said compound is 400–1000 ng/dl.]

[12. The method of claim 8, wherein said compound is administrated parenterally at a dose of 1–2 mg/d.]

[13. The method of claim 8, wherein said compound is administered orally at a dose of 20–100 mg/d.]

[14. The method of claim 8, wherein said compound is administered rectally at a dose of 40–140 mg/d.]

*15. The method of claim 1, wherein said cancer is ovarian cancer.*

*16. The method of claim 1, wherein said cancer is thyroid cancer.*

*17. The method of claim 1, wherein said cancer is testicular cancer.*

*18. The method of claim 1, wherein said cancer is pituitary cancer.*

*19. The method of claim 1, wherein said cancer is prostate cancer.*

*20. The method of claim 1, wherein said cancer is breast cancer.*

* * * * *